US012642576B2

(12) United States Patent
Gershonowitz

(10) Patent No.: US 12,642,576 B2
(45) Date of Patent: *Jun. 2, 2026

(54) APPARATUS AND METHOD FOR FRACTIONAL TREATMENT OF SKIN TISSUE OF A PATIENT AND ELECTRODE FOR USE IN SAID APPARATUS

(71) Applicant: POLLOGEN LTD., Tel Aviv (IL)

(72) Inventor: Amikam Gershonowitz, Tel Aviv (IL)

(73) Assignee: POLLOGEN LTD., Tel Aviv (IL)

( * ) Notice: Subject to any disclaimer, the term of this patent is extended or adjusted under 35 U.S.C. 154(b) by 131 days.

This patent is subject to a terminal disclaimer.

(21) Appl. No.: 18/614,683

(22) Filed: Mar. 24, 2024

(65) Prior Publication Data

US 2024/0293167 A1     Sep. 5, 2024

Related U.S. Application Data

(63) Continuation of application No. 17/324,989, filed on May 19, 2021, now Pat. No. 11,963,710.

(51) Int. Cl.
*A61B 18/14* (2006.01)
*A61B 18/00* (2006.01)

(52) U.S. Cl.
CPC .... *A61B 18/14* (2013.01); *A61B 2018/00077* (2013.01); *A61B 2018/00083* (2013.01);
(Continued)

(58) Field of Classification Search
CPC ................ A61B 18/14; A61B 18/1477; A61B 2018/00077; A61B 2018/00083;
(Continued)

(56) References Cited

U.S. PATENT DOCUMENTS 8,579,896 B2 * 11/2013 Kreindel ............ A61B 18/0218
606/49
2007/0288078 A1 12/2007 Livneh
(Continued)

FOREIGN PATENT DOCUMENTS

KR      10-2010-0065297      6/2010
KR         20130014211      2/2013
(Continued)

OTHER PUBLICATIONS

Search Report and Written Opinion—Corresponding PCT Application No. PCT/IB21/054336, dated Aug. 30, 2021, 13 pages.

*Primary Examiner* — Michael F Peffley
(74) *Attorney, Agent, or Firm* — ISUS INTELLECTUAL PROPERTY PLLC; Anthony Jason Mirabito

(57)          ABSTRACT

The present disclosure relates to an apparatus (1) for fractional treatment of skin tissue of a patient. The apparatus (1) comprises a handpiece with a housing, at least one first electrode (11) and at least one second electrode (15) located on a distal end of the handpiece and an energy source, which is connected to said at least one first (11) and said at least one second (15) electrode. The apparatus (1) is adapted for applying radio frequency (RF) energy to the tissue. The at least one second electrode (15) is arranged on a base plate (13) and the at least one first electrode (11) is or comprises a pin or a needle (11), in particular a microneedle, which penetrates the base plate (13) through a through hole (17). The apparatus (1) further comprises a vacuum chamber (9) behind the base plate (13) and inside of the housing of the handpiece, which is in fluid communication with the at least one through hole (17) provided in the base plate (13) for exerting attraction onto a surface (33) of the skin tissue towards the at least one first electrode (11) and towards the at least one second electrode (15), when the first electrode
(Continued)

(11) and the at least one second electrode (15) is placed in proximity of or is touching the surface (33) of the tissue.

10 Claims, 8 Drawing Sheets

(52) U.S. Cl.
CPC ............... *A61B 2018/00458* (2013.01); *A61B 2018/00577* (2013.01); *A61B 2018/143* (2013.01)

(58) Field of Classification Search
CPC .. A61B 2018/0016; A61B 2018/00291; A61B 2018/00452; A61B 2018/00458; A61B 2018/00577; A61B 2018/143

See application file for complete search history.

(56)                    References Cited

U.S. PATENT DOCUMENTS

| | | | |
|---|---|---|---|
| 2009/0093864 A1* | 4/2009 | Anderson | .......... A61B 18/1477 607/99 |
| 2010/0217253 A1 | 8/2010 | Mehta | |
| 2012/0158100 A1* | 6/2012 | Schomacker | ...... A61B 18/1477 607/101 |
| 2014/0005658 A1* | 1/2014 | Rosenbegr | ............. A61B 18/14 606/33 |
| 2017/0112568 A1 | 4/2017 | Epstein | |
| 2019/0365461 A1* | 12/2019 | Saeki | ................. A61B 18/1206 |
| 2020/0360072 A1* | 11/2020 | Kuang | ................... A61B 18/10 |
| 2022/0054189 A1 | 2/2022 | Wootten | |
| 2022/0072325 A1 | 3/2022 | Ko | |

FOREIGN PATENT DOCUMENTS

| | | |
|---|---|---|
| KR | 101622374 | 5/2016 |
| WO | 2009016634 | 2/2009 |
| WO | 2019046333 | 3/2019 |

* cited by examiner

APPARATUS AND METHOD FOR FRACTIONAL TREATMENT OF SKIN TISSUE OF A PATIENT AND ELECTRODE FOR USE IN SAID APPARATUS

RELATED APPLICATIONS

This application is a continuation of and claims priority to U.S. application Ser. No. 17/324,989, filed May 19, 2021, now U.S. Pat. No. 11,963,710, issued on Apr. 23, 2024, which claims priority to U.S. Provisional Application No. 63/027,762, filed May 20, 2020, the entirety of which applications are hereby incorporated by reference.

FIELD OF THE INVENTION

Generally, the present disclosure relates to apparatuses, devices and methods used for treatment of skin tissue for medical, aesthetic and/or cosmetic procedures. More specifically, the present disclosure relates to an apparatus for fractional treatment of skin tissue of a patient. The present invention also relates to an electrode for use in an apparatus for fractional treatment of skin tissue of a patient. The present disclosure further relates to a method for fractional treatment of skin tissue of a patient.

BACKGROUND

Ablative fractional devices are a method of skin rejuvenation and may be based on micro holes created in a target tissue using an energy source. Ablative fractional devices may include laser and radio frequency (RF) energy.

SUMMARY

It is an objective of the present invention to provide an apparatus for fractional treatment of skin tissue of a patient, the apparatus comprising: a handpiece with a housing; at least one first electrode and at least one second electrode located on a distal end of the handpiece; an energy source, which is connected to said at least one first and said at least one second electrode, wherein the at least one second electrode is arranged on an apertured base plate and the at least one first electrode is or comprises a microneedle which penetrates the base plate through an aperture; a vacuum chamber within the housing of the handpiece, the vacuum chamber being in fluid communication with the at least one aperture provided in the apertured base plate. Wherein the apparatus is configured to apply radio frequency (RF) energy to the skin tissue, and wherein the vacuum chamber is configured to exert a negative pressure force on a surface of the skin tissue towards the at least one first electrode to compress and draw the skin tissue towards the at least one second electrode, when the at least one first electrode and the at least one second electrode is placed in proximity of or is touching the surface of the tissue.

The apparatus, wherein the cross-sectional area, of the microneedle is smaller than the area of the aperture, in order to provide a passage for the negative pressure. The apparatus, wherein the vacuum chamber is airtight sealed and comprises a port for its connection to the negative pressure source. The apparatus, wherein the at least one second electrode surrounds and concentrically encircles by a section thereof, the at least one first electrode. The apparatus, wherein the at least one second electrode, which is preferably one single second electrode, constitutes substantially most of the area of the base plate. The apparatus, wherein the at least one first electrode is a plurality of first electrodes arranged in at least one of the following: at least one row; or in a plurality of row. The apparatus, wherein the plurality of first electrodes has the same polarity and the at least one second electrode has an opposite polarity. The apparatus, wherein the handpiece comprises a main body and a detachable head, and the detachable head comprises the electrodes and the vacuum chamber.

In another objective, the apparatus, wherein the vacuum chamber is defined by the base plate at a front side, a rear plate, and the housing of the handpiece, in particular by the housing of the head, in radial direction. The apparatus, wherein the passage for the negative pressure is configured to produce a negative pressure is applied into the channel created by the microneedles and cause the skin tissue to be compressed and the bottom of the channel to be pulled towards the base plate according to a "sponge effect" and the channel into the skin tissue is ablated by the microneedle. The apparatus, wherein the plurality of rows is arranged on a roller surface.

In yet a further objective, an electrode for use in the apparatus for fractional treatment of skin tissue comprising at least one microneedle having an outside surface, the outside surface being provided with an insulated coating covering an entire shaft of the microneedle, such that only the tip remains electrically conductive. An electrode, wherein in the tip of the microneedle is a blunt flat front tip. The electrode, wherein the electrode comprises a comb-like structure having insulated microneedles with a blunt flat front tip, in particular a flat front tip.

In one objective, there is method for fractional treatment of skin tissue of a patient, the method comprising: providing a handpiece electrical energy source, the handpiece comprising: a housing; at least one first electrode and at least one second electrode located on a distal end of the handpiece, an energy source, which is connected to said at least one first and said at least one second electrode and a vacuum chamber within the housing of the handpiece, the vacuum chamber being in fluid communication with the at least one aperture provided in the apertured base plate; and an energy source, which is connected to the at least one first and the at least one second electrode. Placing a handpiece of a treatment apparatus in close proximity or touching a surface of the skin tissue. Pulling, by the vacuum, the skin tissue towards the at least one first electrode and the at least one second electrode. Supplying the at least one first and the at least one second electrodes with electrical energy. Finally, applying the electrical energy to the skin tissue, wherein ablation is caused in the selected cells in the dermis layer and/or the hypodermis layer of the skin.

The method, wherein touching the surface is executed without application of mechanical pressure by application of force onto the skin tissue using the handpiece. The method, wherein force of the vacuum is configured to decrease the thickness of the at least outer layers of the skin tissue, wherein the total thickness of said at least outer layers of the skin tissue during the application of vacuum is smaller than when said at least outer layers are relaxed.

In a final objective, the method, wherein the at least one first electrode is at least one microneedle and wherein the tissue is compressed against the at least one first electrode and against the at least one second electrode so that a "sponge effect" occurs and the channel into the skin tissue is ablated by the microneedle and due to the compression of the skin the channel is longer than the length of the microneedle. The method, wherein the vacuum is applied in at least one of the following ways: permanently; in intervals;

or pulsating. The method, wherein the level of vacuum, is varied, in particular decreased or switched off when no electrical energy is applied.

BRIEF DESCRIPTION OF THE DRAWINGS

The present disclosure will be described in further detail with reference to the drawing, in which.

DETAILED DESCRIPTION

In general, in connection with RF energy and a microneedle arrangement detailed below, there are two basic configurations. In a monopolar arrangement, a microneedle or a plurality of microneedles has or have one polarity and work together with a separate return plate with a different, particularly opposite, polarity. The return plate is usually positioned on a different zone of the human body, such as on the back or on a leg. In a bipolar arrangement, at least one pair of adjacent microneedles is provided with e.g. a positive polarity at a first one and a negative polarity at a second one of the pair of microneedles. A combination of these two configurations may be utilized by providing a microneedle with a first polarity and a return plate arranged in proximity of the microneedle with a second, particularly opposite, polarity. Common to all these configurations is that the extent of the treatment effect is dependent on the treatment performance provided by the treatment personnel, particularly from a uniform application on a skin surface, and notably a uniform force when pushing a handpiece with the microneedles against the skin surface to be treated.

Figure 1:
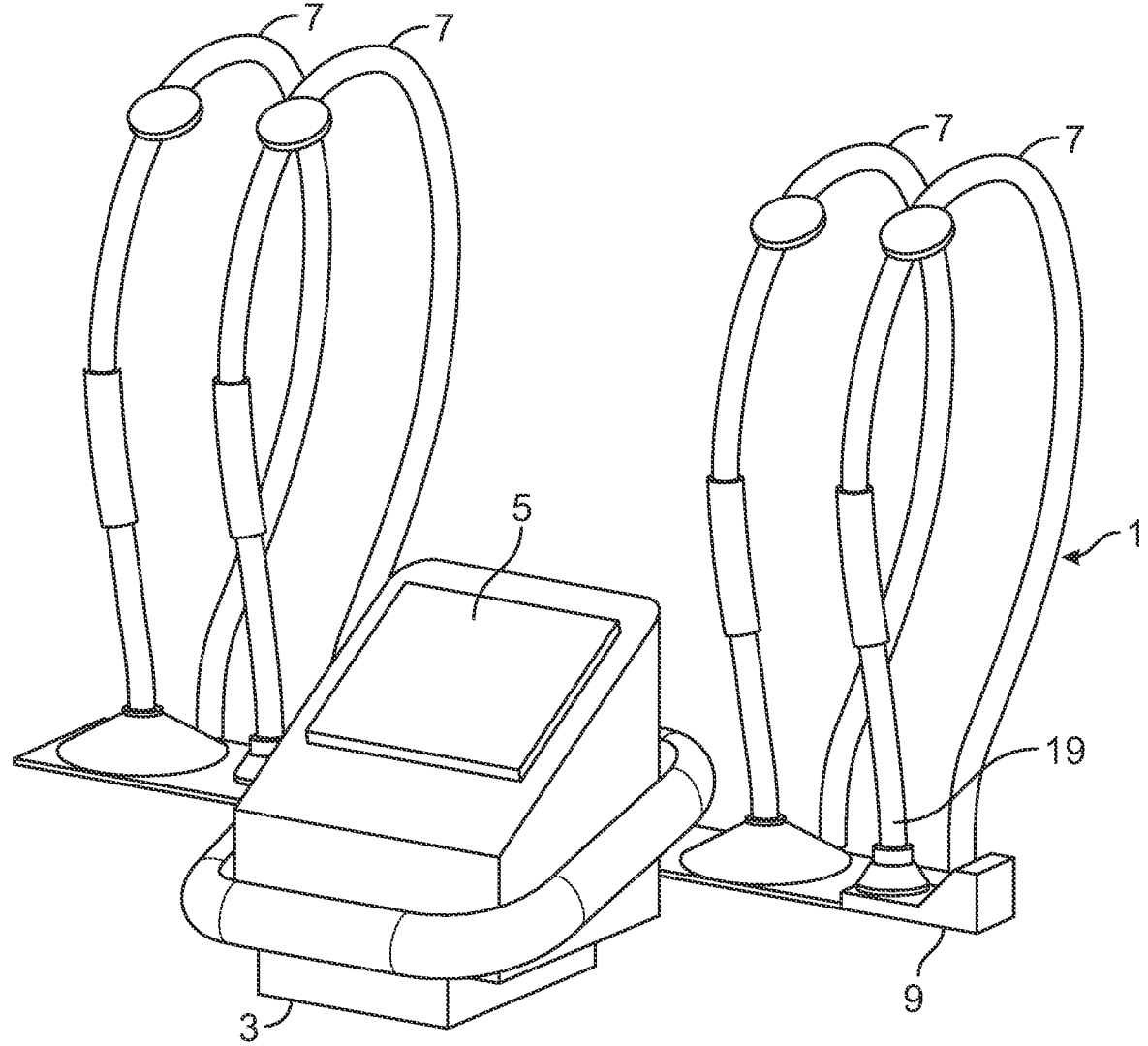
FIG. 1 is a perspective view of an apparatus for cosmetic skin treatment comprising a number of different treatment devices.

FIG. 1 illustrates a perspective view of an apparatus 1 for cosmetic skin treatment, for some embodiments of the current disclosure. In some embodiments, apparatus 1 comprises a basic unit or console 3 including substantial operating components and modules (not shown), such as a power unit for the supply of further electrical units with electrical power, a processor, a memory, and a programmable controller to control operation of the treatment instruments. In some embodiments, the basic unit 3 further comprises a control unit 5 including a touch display (GUI) for an operator, i.e. a treatment personnel, providing inputs to the apparatus 1 for its operation. In some embodiments, multiple, in this example four, treatment instruments 7 are connected to the basic unit 3, each one being provided for a specific type of skin treatment.

In some embodiments, one of the treatment instruments is configured for thermal treatment causing epidermal and dermal effects. Following a thermal the treatment, a healing process is initiated resulting in rejuvenated skin. In some embodiments, to perform said thermal treatment, a treatment head 9 of the respective one of the treatment instruments 7 comprises a two-dimensional array of a plurality of microneedles or pins 11 protruding from a base plate 13 arranged to be positioned and mounted on a distal end of the treatment head 9. In some embodiments, microneedles 11 form first electrodes to be supplied with electrical energy against a second electrode formed by an apertured metallic layer 15 covering the base plate 13 and surrounding the array of microneedles 11. In some embodiments, the base plate is a gold layer. In some embodiments, all of said first electrodes have the same polarity, while the second electrode have a different polarity. In some embodiments, the second electrodes have an opposite polarity to the first electrodes.

Figure 4:
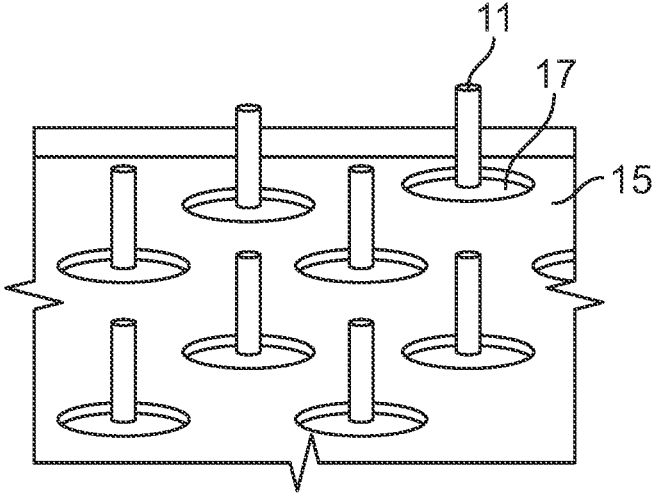
FIG. 4 is a close-up view of a base plate forming an operating area of the head of FIGS. 2 and 3 and including microneedles.

In some embodiments, the first electrodes are isolated from the second electrode by a plurality of small circular apertures 17 in the metallic layer 15, which provides metal-free zones around the first electrodes or microneedles 11. In some embodiments, each of the microneedles 11 is positioned in the center of one of the circular apertures 17. In some embodiments, each of the microneedles 11 is not positioned in the center of one of the circular apertures 17. In some embodiments, the microneedles are a plurality of microneedles of an equal length or depth into the skin. In some embodiments, the plurality of microneedles are different lengths or depth from each other. In some embodiments, the plurality of microneedles are the same shape and cross sectional area. In some embodiments, the microneedles are different shapes and/or cross-sectional area from each other. In some embodiments, the diameter of the circular apertures 17 is made to be greater than the diameter of the microneedles 11, the circular hole 17 provides an annular air gap, and, in this way, an insulation zone between a microneedle 11 in the hole center and the distantly surrounding metallic layer 15. For better visibility, FIG. 4 provides an enlarged illustration of a portion of the base plate 13 with the pair of first and second electrodes formed by microneedles 11 arranged in the centre of circular apertures 17 within the metallic layer 15.

In some embodiments, the first and second electrodes may be supplied with radio frequency (RF) energy by means of a power unit forming an electrical energy source. In some embodiments, the microneedles 11 forming the first electrodes are connected to a first pole of the RF energy source and the metallic layer 15 forming the second electrode is connected to a second pole of the RF energy source. The RF energy applied on skin tissue causes the ablation of the skin below and in contact with the distal end of microneedles 11, which is not only a function of energy intensity but also a function of the duration of the period of time the RF energy is applied.

In some embodiments, the second electrode 15 substantially covers the base plate of the handpiece. For the purposes of this disclosure, a substantial portion of the surface of the base plate shall be understood, which is preferably more than 50%, more preferably more than 70%, even more preferably more than 85%, of the entire surface of the base plate. More specifically, the second electrode is one single second electrode, which may be a flat electrode that covers a relevant portion of the base plate in a two-dimensional way. Particularly, the second electrode covers the whole base plate leaving only a section or sections unfilled, which is or are occupied by the first electrode, preferably by further providing a distance between first and second electrodes.

Figure 2:
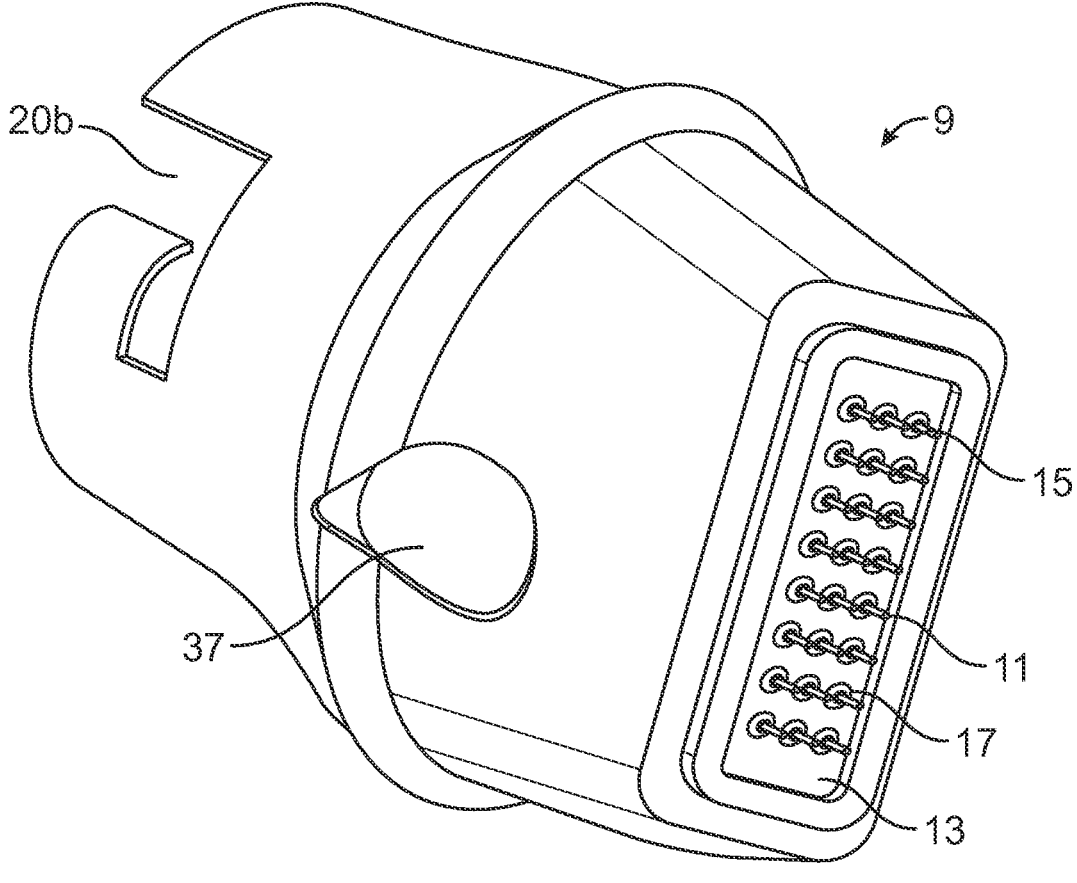
FIG. 2 is a perspective view of a first side of a head of one of the treatment devices according to FIG. 1.
Figure 3:
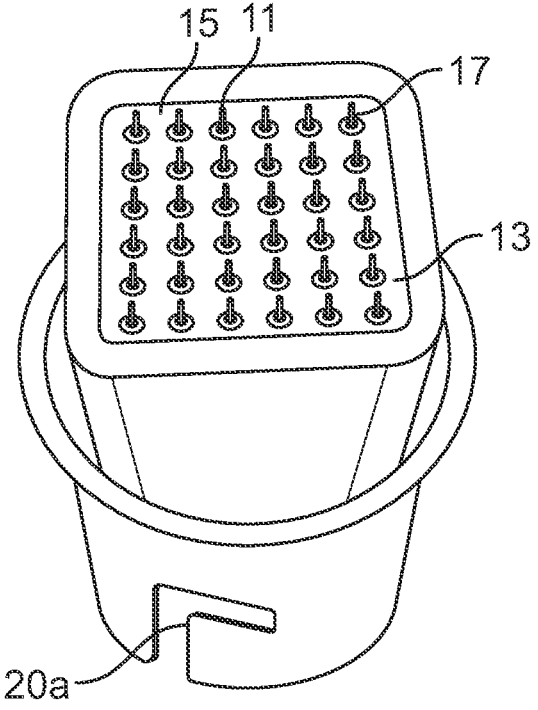
FIG. 3 is a perspective view of a second side of the head according to FIG. 2 in an upright position.

In some embodiments and as also indicated by FIGS. 1 to 3, the treatment head 9 is detachably connected to a main body 19 of the treatment instrument 7 by a first and a second bayonet fastening means 20a, 20b, with the second bayonet fastening means 20b being arranged diametrically opposite to the first bayonet fastening means 20a at a rear side of the treatment head 9. The first and second bayonet fastening means 20a, 20b are configured to engage with respective collaborating fastening means (not shown) at the main body 19. In some embodiments, the treatment head 9 is detachably connected to main body 19 of the treatment instrument 7 by any suitable method in the art.

Figure 5:
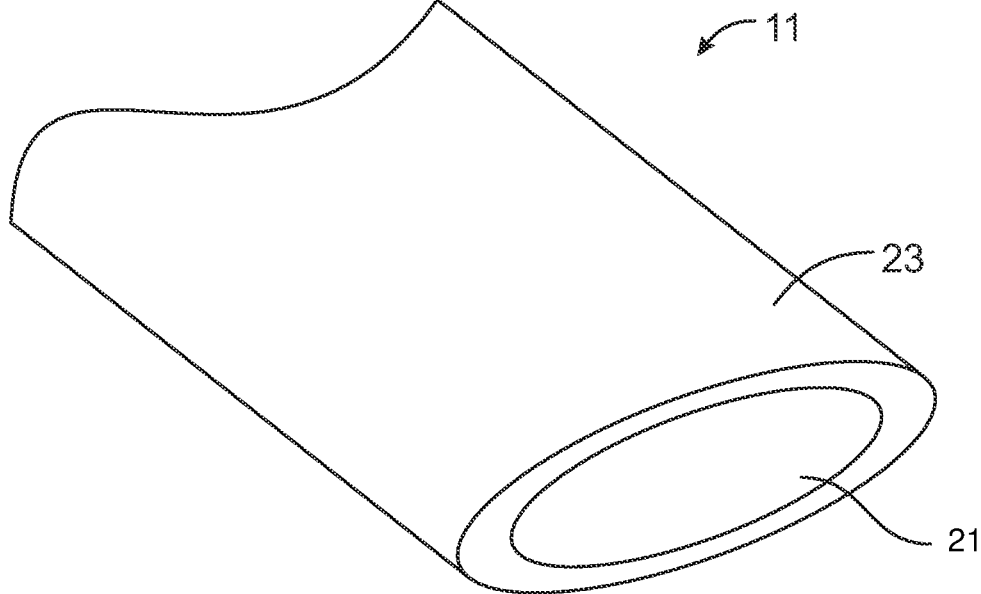
FIG. 5 is a perspective view of a distal end portion of one of the microneedles according to FIG. 4.

FIG. 5, illustrates a frontal part of one of the microneedles 11, of some embodiments of the current disclosure. In some embodiments the microneedle 11 is not a needle with a pointed and/or sharp tip. In some embodiments, the distal end of the microneedle is a cone shape tip. In some embodiments, the microneedle 11 of apparatus 1 comprises a flat tip 21, and the shape of a microneedle 11 more resembles that of a cylindrical pin. In some embodiments, an electrically insulated coating 23 of the microneedle 11, extends over the entire microneedle shaft and the flat tip 21 is uncovered from the insulated coating 23 not marked on drawings. In some embodiments, the insulated coating 23 combined with the uncovered flat tip 21 results in an electric field build up only between the uncovered flat tip 21 of each microneedle 11 and the surrounding metallic layer. While shown in FIG. 4 as being of circular cross-sectional shape, it is to be understood that any suitable shape may be employed.

Figure 6A:
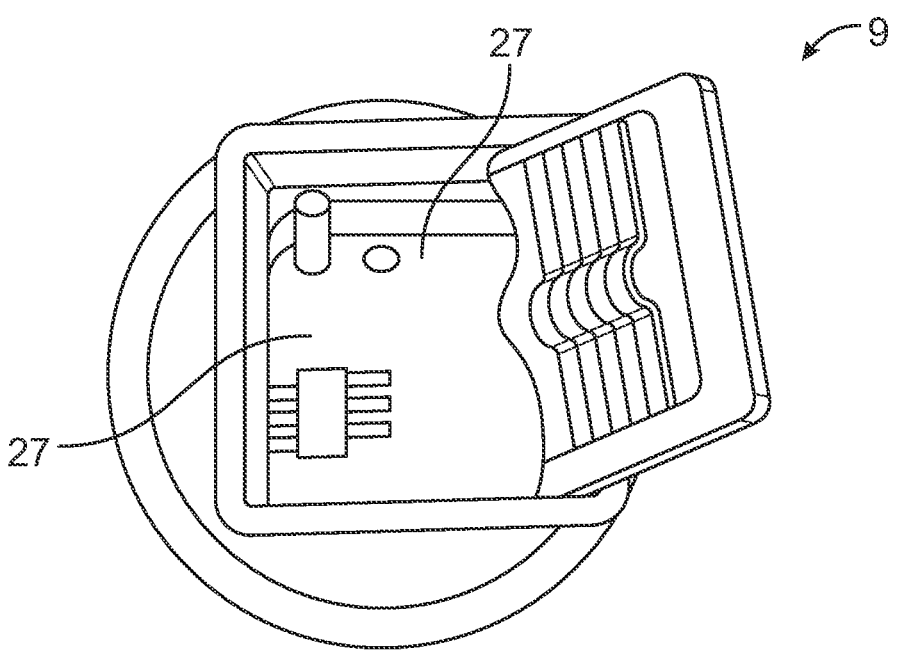
FIG. 6a is a perspective view of the head similar to the viewing direction as in FIG. 3, however, with the base plate detached and pivoted into a swung-out position.
Figure 6B:
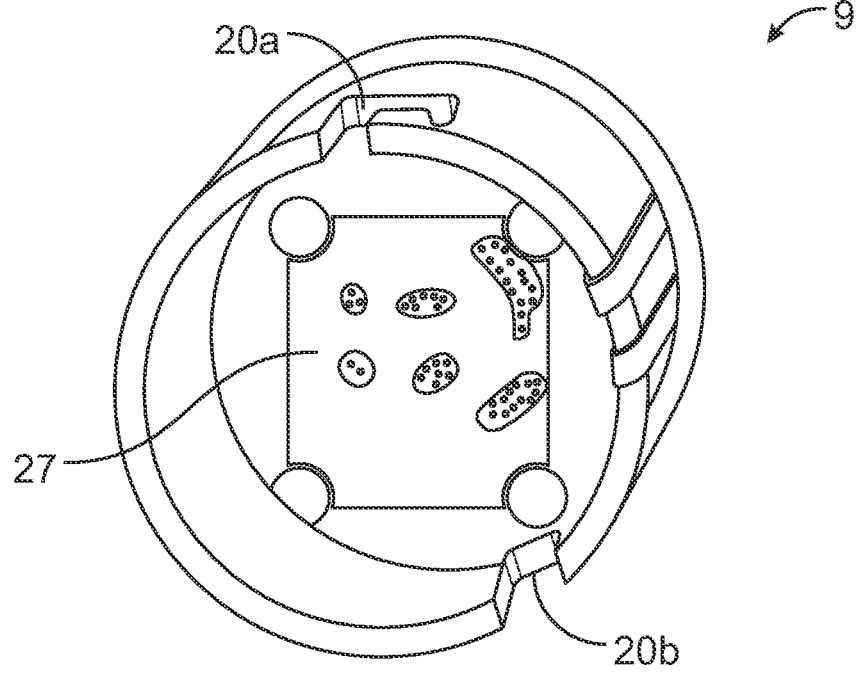
FIG. 6b is a perspective bottom view of the head according to FIGS. 2 and 3.
Figure 7:
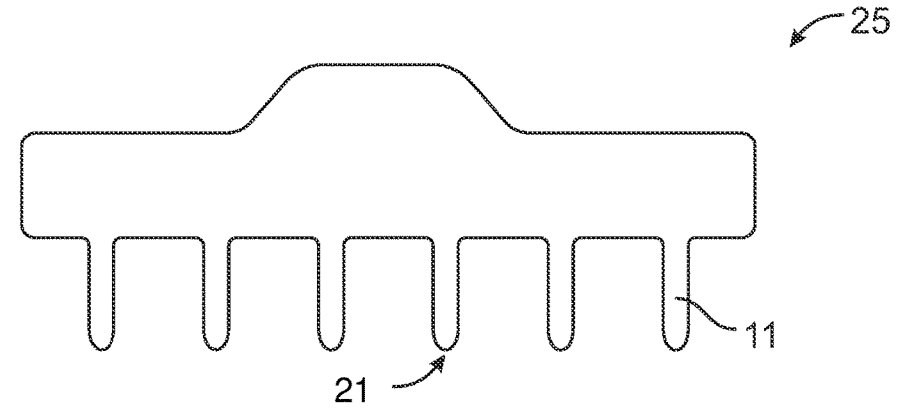
FIG. 7 is a front view of a component of the base plate visible in FIG. 6a forming an arrangement of connected microneedles.

FIGS. 6a and 6b provide a more detailed view of the interior of the treatment head 9, according to some embodiments of the current disclosure. FIG. 6a illustrates the interior of the head from the front end of the treatment head 9. In some embodiments, the base plate 13, which is regularly arranged at and covering this front end, is shown in a detached and pivoted into a swung-out position. In some embodiments, and as readily understandable by a skilled person from this illustration, the base plate 13 comprises a first printed circuit board with an arrangement of parallel aligned microneedle combs 25, each one thereof themselves constituting an arrangement of connected microneedles 11. In some embodiments, the microneedles 11 are equidistantly arranged on each one of the combs 25 and the distance between two adjacent combs 25 is at least approximately in the same value as the distance between two adjacent microneedles 11 on the same comb 25, so that an equidistant two-dimensional array of microneedles 11 is provided. In some embodiments, non-equidistant or arrays of needles having different lengths, interchangeably or otherwise spread, arrangements are configured.

In some embodiments, and as illustrated in FIG. 6a, a front view onto a rear plate 27, the rear plate comprises a second printed circuit board, which is included in the interior of the treatment head 9. In some embodiments, the rear plate 27 with the second printed circuit board, the rear side thereof being shown in FIG. 6b, comprises an electronic circuit, and is arranged a distance from the base plate 13 and in a parallel arrangement thereto. With this arrangement, the base plate 13, the rear plate 27 and the housing of the treatment head 9 may form a chamber within the interior of the treatment head 9. Moreover, in some embodiments, both the base plate 13 and the rear plate 27 are sealed against the housing of the treatment head 9, so that the chamber is a sealed chamber 9. In some embodiments the base plate 12 and the rear plate 28 are sealed against the housing of the treatment head by silicone glue.

In some embodiments, a vacuum is created inside of the sealed chamber 9 via a vacuum port 31 (see FIG. 2) at the housing of the treatment head 9, which vacuum port 31 is connected via a vacuum tube (not shown) to a negative pressure source (not shown), which may be arranged inside of the basic unit 3. In some embodiments, since the sealed chamber 9 is located behind the base plate 13 (when looking from the outside) and also behind the array of microneedles 11, and since the microneedles 11 are surrounded by annular air gaps provided by the circular apertures 17, the sealed chamber 9 is in fluid communication with the ambient air through said air gaps, so that the vacuum is applied to each one of the air gaps, i.e. adjacent or surrounds to each one of the microneedles 11.

In some embodiments, the vacuum or negative pressure source is arranged in the apparatus distant from the handpiece and may be a suction pump or the like. In some embodiments, the negative pressure source/the suction pump is connected with the vacuum chamber by means of a connecting tube. In some embodiments, the connecting tube for the negative pressure source is configured in a combined supply pipe further including means for supplying electrical energy to the handpiece.

In some embodiments, the device comprises a pressure sensor configured to measure the pressure in the vacuum chamber and transmit the information into a controller. In some embodiments, the vacuum level in the vacuum chamber is maintained in a low, sensing, level so that when contacting a surface of the skin tissue with a handpiece of a treatment apparatus, due to the proximity of the skin which tends to block the holes in the return plate through which the negative pressure reaches the skin, the negative pressure in the vacuum chamber decreases. Decreased pressure measurements by the pressure sensor may indicate handpiece placement on a target tissue and may cause the controller to further increase the power to the vacuum pump in order to produce treatment vacuum level and initiate a RF treatment.

Figure 8:
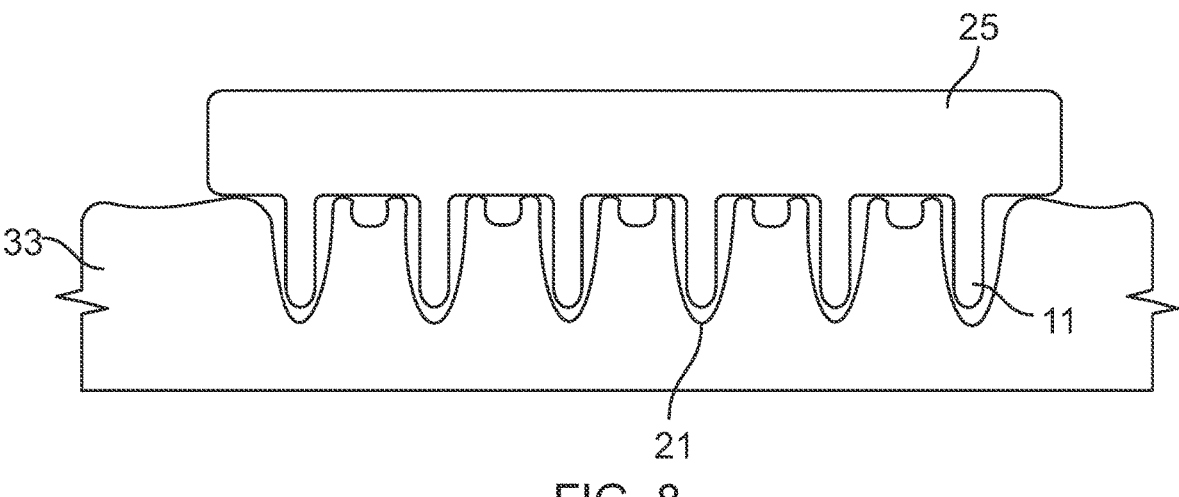
FIG. 8 is an illustration of the component according to FIG. 7 place on a skin surface at the time of treatment initiation.

By way of example, a thermal skin treatment process will be described. When the tips 21 of the microneedles 11 are flat and, and not configures alone for penetration into the skin surface 33 when no electrical energy is supplied to the first and second electrodes, the skin surface 33 contacts the tips 21 of the microneedles 11 and return plate 15, which deform the skin by building wave troughs at the contacting areas. Therefore, contacting of the surface is executed without the application of mechanical forcing of the handpiece onto the skin tissue surface to force the first and/or second electrodes into the tissue surface. FIG. 8 illustrates this effect by showing only one microneedle comb 25 contacting and deforming the skin surface 33, in some embodiments of the current disclosure.

In some embodiments, the effect onto the skin surface 33, when the treatment head 9 with the two-dimensional array of microneedles 11 are contacting the skin surface 33. If the treatment head 9 is pushed against the skin surface 33 with more pressure and/or when the vacuum is turned on, the sections of the skin surface 33 between the contacting areas with the tips 21 of the microneedles 11 will be pulled into contact with the metallic layer 15 through the vacuum force, so that the skin surface 33 closes the contact between the first electrodes, i.e. the tips 21 of the microneedles 11, and the second electrode, i.e. the metallic layer 15.

Figure 9A:
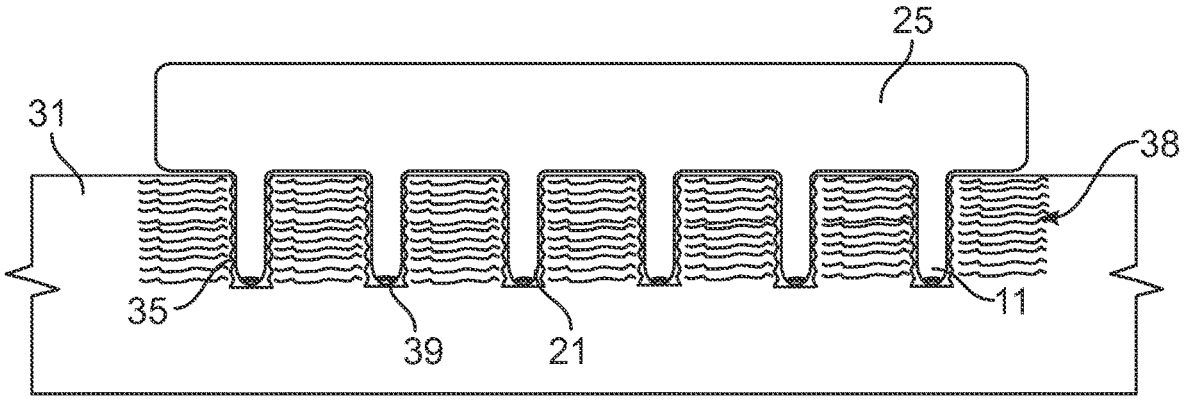
FIG. 9a is an illustration of a later stage of the treatment process initiated as illustrated in FIG. 8, while the vacuum is still switched on, FIG. 9b is an illustration of a later stage of the treatment process initiated as illustrated in FIG. 8, while the vacuum is switched off.
Figure 9B:
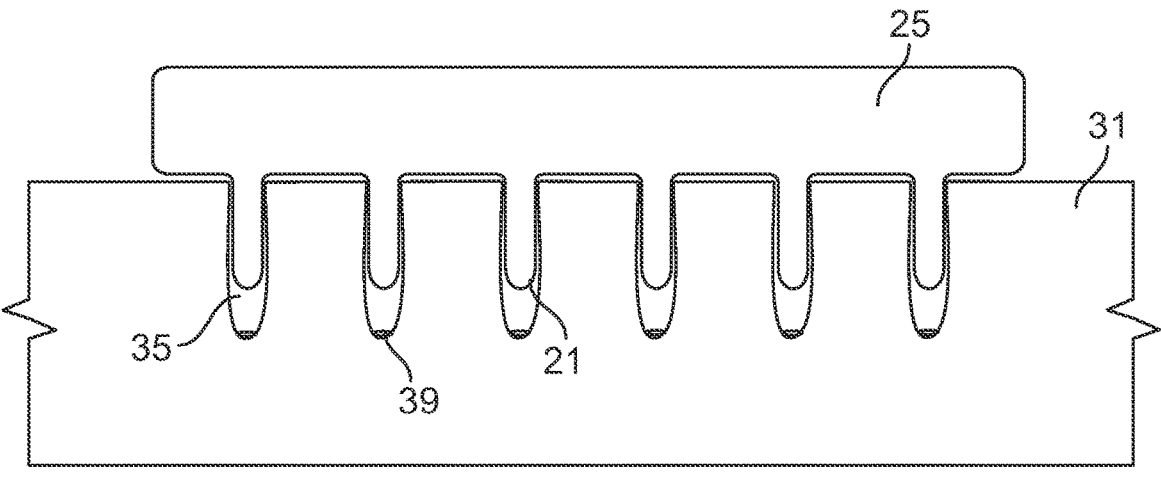

When the RF energy is turned on, a high-density RF field is created at the tips 21 of the microneedles 11 with the effect of performing an ablation of the tissue contacting the tips 21. This ablation disconnects the electrical contact between tips 21 and plate 15 and, as a result, the skin moves up toward the tips 21 due to its elasticity and re-closes the electrical contact between tip 21 and plate 15. In some embodiments, this afore-described process is continuously repeated and the skin tissue is gradually ablated until the skin surface is levelled and reaches plate 15. As can be seen in FIGS. 9*a* and 9*b*, in an advanced stage of the process, in some embodiments, the microneedles 11 penetrate into the skin tissue causing recesses 35 therein.

The upper layer of the skin is the stratum corneum, which is a layer of dry skin cells. The layer below the stratum corneum is the epidermal layer, which has more vital cells with some wet extra cellular matrix. Therefore, the impedance of the stratum corneum is much higher than the impedance of the layer below due to water content. Consequently, in some embodiments, the treatment process of the described apparatus 1 is characterized by an initial high energy pulse configured to ablate the cells of the stratum corneum and, thereafter, the system continues with a supply of lower energy pulses, due to the reduced impedance when the epidermal layer has been reached. In some embodiments, an initial at least one shorter time energy pulse compared with longer energy pulse for treatment is used to ablate the cells of the stratum corneum.

Moreover, the vacuum applied to the annular air gaps on the base plate 13 as well as on the metallic layer 15 forming the second electrode, causes a negative pressure on a skin surface, so that the afore-described treatment process is enhanced. In some embodiments, the vacuum in the scaled chamber 9, or the related negative pressure applied to the annular air gaps, respectively, allows the treatment personnel to place the treatment head 9 on the skin surface 33, which causes the skin to be put into a preloaded state, i.e. the negative pressure pulls the skin surface 33 and the skin tissue below the surface 33 against the microneedles 11 and the metallic layer 15. This process compresses, as shown in FIG. 9*a* as reference numeral 38 the skin tissue especially below the flat tips 21 of the microneedles 11. Similar to the procedure without application of vacuum, the intention and configuration of the forces applied by the treatment personnel as well as the design of the tips 21 of the microneedles 11 is not to penetrate the skin due to any of such settings. Penetration into the skin only occurs due to ablation once the RF energy is supplied to the first and second electrodes, but not as a consequence of mechanical insertion of the microneedles 11 into the skin. Instead, there is a penetration driven by RF energy and related ablation of tissue causing a gradual decompression of the preloaded skin by progressive creation of space in the ablated areas.

The difference between the ablation and penetration process with and without application of vacuum is the magnitude of skin compression, which skin is preloaded against the tips 21 of the microneedles 11 in an enhanced way. In some embodiments, since the vacuum is activated during the whole treatment process and continues to exert attraction onto the skin and/or to pull the skin against the tips 21 and to compress 38 the skin tissue particularly below the tips 21, the effective penetration depth, once the tissue is decom-pressed, is increased and the holes drilled and formed by the microneedles 11 in the skin are longer than the holes drilled without vacuum and also longer than the length of the microneedles 11. Once the vacuum is turned off, together with or after RF energy termination, the skin relaxes and returns to its non-compressed state, as may be seen in FIG. 9*b*.

In some embodiments, and as previously mentioned, the shafts of the microneedles 11 are entirely insulated, i.e. not, as in the past, insulated except near to the distal tip of the microneedles a with an omission of insulation only in an area around the tips of the microneedles 11. Rather, here only a flat front face of the blunt tip 21 is non-insulated. Therefore, no electric field is generated in radial directions originating from the shaft surface, i.e. the outer surface of a cylindrical microneedle 11, but only an electric field originating from the flat tip 21 surface.

With this non-sharp, flat and insulated design of the microneedles 11, the treatment process with penetration due to application of RF energy is executed in the same way as previously described. However, an advantage of this RF penetration process using microneedles 11 with entirely insulated shafts is that there is little to no collateral thermal damage to the tissue along the outer surface of the needles, which is in contact with the shaft of the microneedles 11. Such kind of collateral damage occurs in the case of non-insulated and only partly insulated shafts of the microneedles 11.

In some embodiments, with the use of non-insulated microneedles 11, a coagulation zone is known to be created starting from the top, i.e. next to the first electrode 11 tip 21, and grows down as the treatment with RF energy progresses. In some embodiments, the coagulation zone grows deeper into the tissue as RF energy is delivered to the microneedles 11. The more RF energy is supplied, the greater the coagulation zone will be. This process continues even once the entire microneedles 11 have reached their final depth into the tissue and continues until RF energy supply is terminated. In summary, the process is terminated only by termination of RF energy supply. Moreover, in some embodiments, the shape of the generated recesses is cone-shaped, as seen in FIG. 9B, with extended coagulation areas around the microneedles 11 at and close to the uppermost skin layers.

In some embodiments, with an entirely insulated shaft the coagulation zone does not grow even if the RF energy supply is continued. The treatment has an "inherent" termination point. Further, as is also visible in FIGS. 9*a* and 9*b*, there is little to no thermal damaged zone along the outer surface of the shafts of the microneedles 11 since the "feed motion" into the skin tissue caused by the electric field originating from the flat tip 21 acts or projects only axially. In some embodiments, the recesses 35 produced by the RF penetration process are at least approximately of cylindrical shape with a diameter only slightly larger than the diameter of the microneedles 11.

Therefore, once the penetration is terminated, the structure of penetrated microneedles 11 inside of the generated recesses 35 is like the illustration in FIGS. 9*a* and 9*b*, i.e. without any coagulation along the needle but only with a portion of tissue 37 below the flat tip 21. Moreover, once microneedles 11 are fully inserted into the skin, the RF power to the electrodes may be lowered to a sub-ablative level in order to create fractional thermal affected zones 39 at the bottom on recesses 35.

In some embodiments, when only the flat tips 21 of the microneedles 11 are active, less energy is required for the treatment process than the energy required in the case of non-insulated microneedles 11, which cause a "waste of energy" due to the energy expended in an ablation of large-sized recesses in the skin tissue.

In some embodiments, when the vacuum is utilized, as discussed, the skin tissue is drawn towards the base plate, and shorter needles may be used than in other devices using longer needles or pins, yet still achieve as deep, if not deeper, penetration into the skin tissue without the same degree of pain or at least discomfort as in devices having longer needles.

In this context, and by way of example, the vacuum which is applied during the treatment stage as shown in FIG. 9*a* "works" into the channels formed by the pins and pulls the bottom of the channels towards the base plate. Due to the flexibility of the skin, a "sponge effect" occurs, whereby the skin laterally to the channel walls is compressed 38 in direction length to the pins.

FIG. 9*b* is an illustration of a later stage of the treatment process initiated as illustrated in FIG. 8, while the vacuum is switched off, according to some embodiments of the current disclosure. Once the negative pressure does not pull the bottom of the channels towards the base plate any longer the channels fill with air, bodily fluids or other liquids if provided during the procedure and due to the flexibility of the skin tissue the compressed skin 38 expands pushing the bottom of the channels away from the base plate. Therefore, the skin is decompressed the channels in the skin that have been formed by the pins are much longer than the pins.

Figure 10:
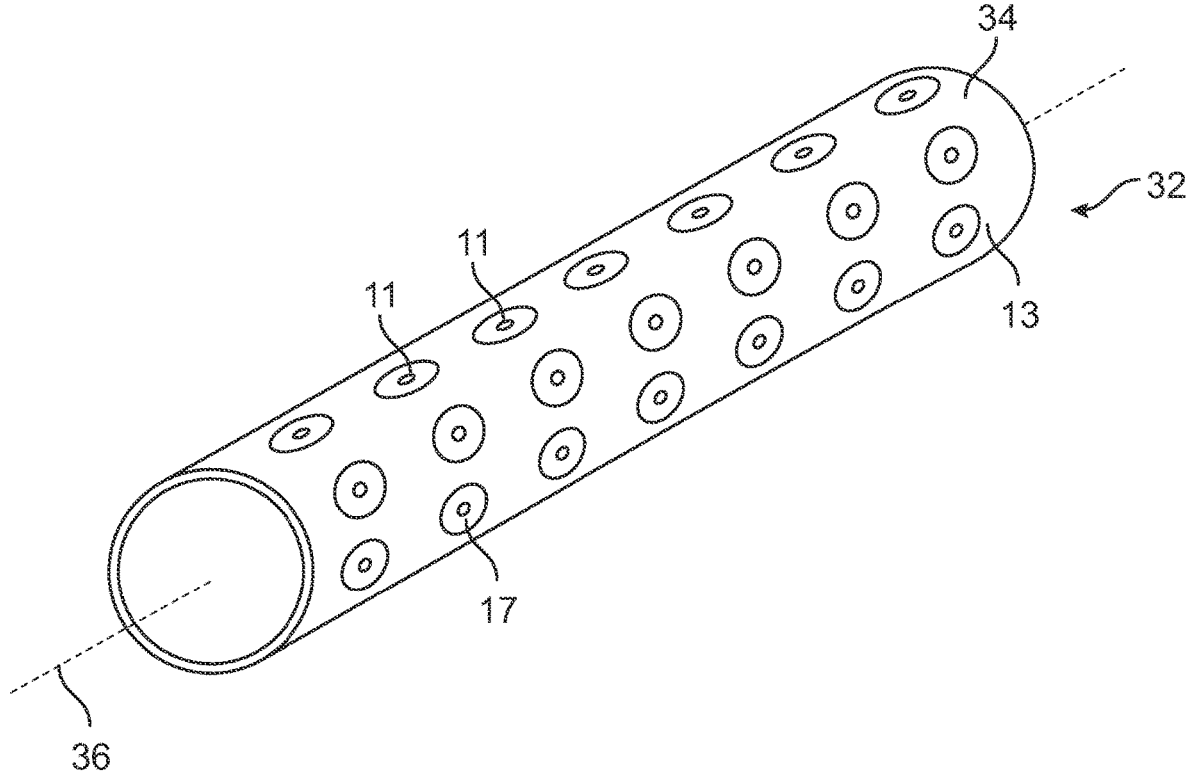
FIG. 10 shows a functional sketch of an embodiment having the array of microneedles arranged on a roller.

FIG. 10 shows a functional sketch of some embodiments having the array of needles arranged on a roller 32. As illustrated, in some embodiments, a roller 32 comprises a cylindrical surface 34, instead of a plane flat surface as shown in FIGS. 2 and 3. In some embodiments, the roller 32 is derived and acts like the base plate 13 by bending it to become the lateral surface 34 of the cylindrical formed roller 32. In some embodiments, the roller 32 has an axis 36 which may be supported by the handpiece. In some embodiments the roller spins around the axis 36 allows a rolling over the skin surface 33 of the patient during treatment.

In some embodiments, the plurality of rows is arranged on a roller surface and with such an arrangement, a continuous skin tissue or skin surface treatment of an area larger than the treatment area of the handpiece without any explicit lifting of the handpiece from the surface of the skin tissue and repositioning the handpiece may be possible. Rather, the handpiece may be moved along the skin surface to be treated, while the treatment process is continuously executed.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An apparatus for treatment of skin tissue of a patient, the apparatus comprising:
   a handpiece with a housing;
   at least one first electrode and at least one second electrode located on a distal end of the handpiece;
   an electrical energy source, which is connected to said at least one first and said at least one second electrode, wherein the at least one second electrode is arranged on an apertured base plate and the at least one first electrode distally penetrates the apertured base plate through at least one aperture in the apertured base plate, wherein the cross-sectional area of the at least one aperture is larger than the area of the at least one first electrode; and the apparatus being configured to:
      apply ablative radio frequency (RF) energy from the electrical energy source to the skin tissue, wherein said at least one first electrode is in the form of a pin or needle having a flat and blunt conductive distal end that does not penetrate into the skin surface when no electrical energy from the electrical energy source is supplied; and
      ablate the skin tissue in contact with the flat and blunt conductive distal end and drill a hole in the skin tissue when the ablative radio frequency energy is applied.

2. The apparatus according to claim 1, wherein the at least one second electrode surrounds and concentrically encircles the at least one first electrode.

3. The apparatus according according to claim 1, wherein the at least one second electrode, which is preferably one single second electrode, constitutes substantially most of the area of the base plate.

4. The apparatus according to claim 1, wherein the at least one first electrode is a plurality of first electrodes arranged in at least one of the following:
   at least one row; or
   a plurality of rows.

5. The apparatus according to claim 4, wherein the plurality of first electrodes has the same polarity and the at least one second electrode has an opposite polarity.

6. The apparatus according to claim 4, wherein the handpiece comprises a main body and a detachable head comprising the electrodes.

7. The apparatus according to claim 4, wherein the plurality of first electrodes is arranged in a plurality of rows on a roller surface.

8. The apparatus according to claim 1, wherein the at least one first electrode comprises at least one pin or needle having an outside surface, the outside surface being provided with an insulated coating covering an entire shaft of the pin or needle such that only the tip remains electrically conductive.

9. The apparatus according to claim 8, wherein the electrode comprises a plurality of the pins or needles in the form of a comb-like structure.

10. A method for treatment of skin tissue of a patient, the method comprising:

providing a handpiece comprising a housing; at least one first electrode and at least one second electrode located on a distal end of the handpiece, the at least one second electrode is arranged on an apertured base plate and the at least one first electrode distally penetrates the apertured base plate through at least one aperture in the apertured base plate, wherein the cross-sectional area of the at least one aperture is larger than the area of the at least one first electrode providing an electrical energy source, which is connected to said at least one first and said at least one second electrode;

placing the handpiece in close proximity or touching a surface of the skin tissue, supplying the at least one first and the at least one second electrodes with electrical energy; and applying the electrical energy from the electrical energy source to the skin tissue, wherein said at least one first electrode is in the form of a pin or needle having a flat and blunt conductive distal end that does not penetrate into the skin surface when no electrical energy from the electrical energy source is supplied and the at least one first electrode is configured to ablate the skin tissue in contact or close proximity to the flat and blunt conductive distal end and drill a hole in the skin tissue when the ablative radio frequency energy is applied.

\* \* \* \* \*